US005186864A

United States Patent [19]

Commandeur et al.

[11] Patent Number: 5,186,864

[45] Date of Patent: Feb. 16, 1993

[54] SYNTHESIS OF DIELECTRIC LIQUIDS BY IMPROVED FRIEDEL-CRAFTS CONDENSATION

[75] Inventors: Raymond Commandeur, Vizille; Noelle Berger, Ecully; Pierre Jay, Saint Didier au Mont d'Or; Jacques Kervennal, Lyons, all of France

[73] Assignee: Atochem, Puteaux, France

[21] Appl. No.: 597,030

[22] Filed: Oct. 15, 1990

[30] Foreign Application Priority Data

Oct. 13, 1989 [FR] France ............................ 89 13451

[51] Int. Cl.5 ........................ C07C 1/26; C07C 2/02; H01B 3/22; H01B 3/24

[52] U.S. Cl. ................................ 252/581; 252/570; 585/25; 585/426; 585/428; 585/429; 570/199

[58] Field of Search ................ 252/570, 581; 585/25, 585/426, 428, 429; 570/199

[56] References Cited

U.S. PATENT DOCUMENTS

| | | | |
|---|---|---|---|
| 2,012,302 | 8/1935 | Clark et al. | 570/199 |
| 3,006,972 | 10/1961 | Fields et al. | 570/199 |
| 4,438,027 | 3/1984 | Mathais et al. | 570/199 |
| 4,523,044 | 6/1985 | Commandeur et al. | 585/11 |
| 4,929,784 | 5/1990 | Klinkmann et al. | 585/422 |

FOREIGN PATENT DOCUMENTS

| | | |
|---|---|---|
| 533352 | 4/1958 | Belgium . |
| 931987 | 3/1948 | France . |
| 2510135 | 1/1983 | France . |

*Primary Examiner*—Christine Skane

*Attorney, Agent, or Firm*—Burns, Doane, Swecker & Mathis

[57] ABSTRACT

Dielectric liquids are prepared by (a) Friedel-Crafts condensing at least one aromatic halide with at least one aromatic compound in the presence of a catalytically effective amount of ferric chloride, and thereafter deliberately avoiding any downstream destruction/neutralization and/or washing of such ferric chloride catalyst, (b) optionally, removing unreacted reactants from the medium of reaction, and (c) recovering from such medium of reaction a purified dielectric liquid; the subject process is thus environmentally improved by avoiding the generation of aqueous solutions containing contaminating amounts of objectionable organic compounds.

16 Claims, No Drawings

SYNTHESIS OF DIELECTRIC LIQUIDS BY IMPROVED FRIEDEL-CRAFTS CONDENSATION

BACKGROUND OF THE INVENTION

1. Field of the Invention

The present invention relates to the improved synthesis of dielectric liquids and more especially, to an improved synthesis of dielectric liquids via a Friedel-Crafts condensation in the presence of a ferric chloride catalyst.

2. Description of the Prior Art

European patent application EP 8,251 describes dielectric liquids having the formula

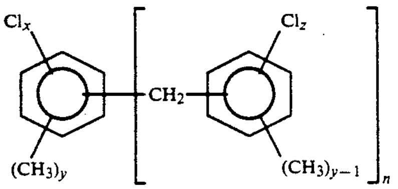

in which n, x, y and z have the value 1 or 2. These compounds can be prepared by condensing:

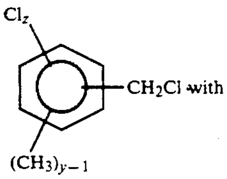
with
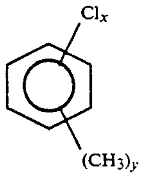

in which n, x, y and z are as defined above, in the presence of a Friedel-Crafts catalyst. After condensation, the catalyst is destroyed, for example by adding a dilute aqueous solution of hydrochloric acid, followed by a washing of the organic phase.

SUMMARY OF THE INVENTION

It has now unexpectedly and surprisingly been determined that, if ferric chloride is employed as the Friedel-Crafts catalyst in the above condensation reactions, it is no longer required to effect destruction of the catalyst. Nor is it necessary to wash the organic phase.

Thus, a major object of the present invention is the provision of an improved, far simpler process for the synthesis of dielectric liquids having the same properties as those prepared by the conventional prior art catalyst destruction/wash stage process, but which permits eliminating said catalyst destruction and washing stages.

It too has been determined that, if other catalysts are used, for example aluminum chloride, the requirements of catalyst destruction and washing cannot be avoided. Indeed, if such parameters are omitted, the final products are unsuited for use as dielectric liquids. This finding is believed to very favorably influence the state of the art. Thus, given that the destruction of the Friedel-Crafts condensation catalyst is typically carried out using an aqueous solution, thus producing an aqueous solution containing organic compounds, and that this aqueous solution, even though the organic compound content thereof is low, must be treated from an environmental standpoint before it can be discharged to waste, the process of the invention provides an attractive alternative.

Patent application EP 136,230 describes dielectric fluids which are polyarylalkane oligomers prepared by condensing benzyl chloride $C_6H_5CH_2Cl$ and benzylidene chloride $C_6H_5CHCl_2$ with toluene in the presence of a Friedel-Crafts catalyst. It has now been found, in the case of this process also, when ferric chloride is used as the catalyst, the washing stage can be avoided, but nonetheless a reaction product is produced that is well suited for dielectric applications.

Briefly, the present invention features a simple improved process for synthesizing dielectric liquids by Friedel-Crafts condensation, comprising (a) condensing an aromatic halide with an aromatic compound in the presence of a catalytically effective amount of ferric chloride, while avoiding any downstream destruction of the catalyst, whether by neutralization as washing, or any combination thereof, (b) optionally, distilling off any excess reactants, and (c) distilling therefrom at least certain of the condensation products and converting same into a useful dielectric liquid.

DETAILED DESCRIPTION OF THE PREFERRED EMBODIMENTS OF THE INVENTION

More particularly according to the present invention, it will of course by appreciated that the basic process sequence, albeit including the catalyst neutralization/-washing step, is known to this art and is described, for example, in EP 8,251. The condensation of stage (a) is a classical Friedel-Crafts reaction.

By "aromatic halide" are intended, for example, the alkylbenzenes or (polyalkyl)benzenes containing at least one halogen at a benzyl position on the alkyl radical, with the benzene nucleus either being substituted or unsubstituted, for example, in addition to the halogenated alkyl radical, being substituted by halogen atoms, alkyl radicals having up to three carbon atoms, or nitrile or $NO_2$ substituents.

The alkyl radicals substituted by at least one halogen atom may be identical or different and may have up to three carbon atoms.

Such aromatic halides include, for example, the compounds of the formulae:

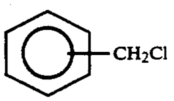

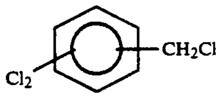

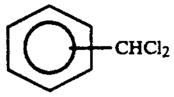

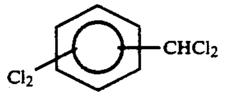

-continued

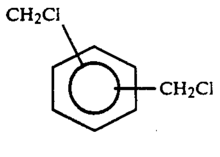

(wherein the basic nucleus may be substituted by 1 or 2 chlorine atoms)

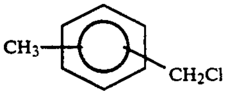

(wherein the basic nucleus may be substituted by 1 or 2 chlorine atoms)

These aromatic halides are condensed with aromatic compounds. By "aromatic compounds" are intended benzene and benzene substituted by one or more alkyl radicals which may be identical or different and which have up to 8 carbon atoms, by halogen atoms or by nitrile or $NO_2$ substituents.

Such aromatic compounds include, for example, benzene, toluene, xylene and compounds of the formulae

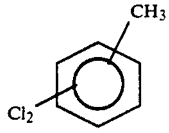

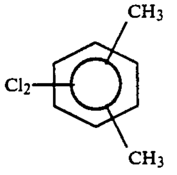

In actual practice, the condensation itself is typically carried out at a temperature ranging from 50° C. to 150° C. The amount of ferric chloride advantageously ranges from 50 ppm by weight of the reaction medium.

A stoichiometric excess of the aromatic halide or of the aromatic compound can be employed in the condensation stage. Depending on the proportions of the various reactants, different condensation products are produced, which are themselves mixtures. In most cases, it may be necessary to distill off the excess reactants because these materials, even in admixture with the condensation products, do not have proper dielectric properties or cannot be employed as dielectrics because of the excessively high volatility thereof.

All, or at least one, of the condensation products is/are recovered in stage (c). Indeed, a mixture of products is frequently produced during the condensation (stage (a)).

For example, when benzyl chloride is condensed with toluene, an oligomer A is produced, which is a mixture of isomers of the formula:

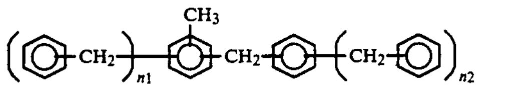

in which $n_1$ and $n_2$ have the value 0, 1 or 2 and $n_1+n2$ is less than or equal to 3.

The mixture may contain the condensation product wherein $n_1$ and $n_2=0$, designated a benzyltoluene (MBT), and the product in which $n_1+n_2=1$, designated a dibenzyltoluene (DBT).

When benzylidene chloride $C_6H_5CHCl_2$ is condensed with toluene and DBT, an oligomer B is produced, which is a mixture of isomers of the formula:

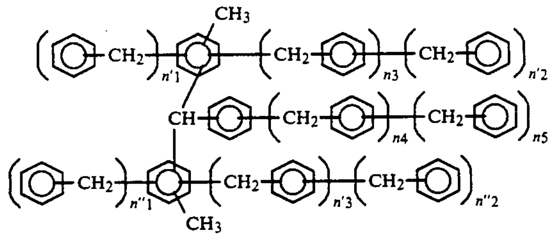

in which $n'_1$, $n''_1$ and $n_4$ have the value 0, 1 or 2, $n'_2$, $n''_2$, $n_3$, $n'_3$ and $n_5$ have the value 0 or 1, and with the sum $n'_1+n''_1+n'_2+n''_2+n_3+n'_3+n_4+n_5$ being less than or equal to 2.

When a mixture of $C_6H_5CH_2Cl$ and $C_6H_5CHCl_2$ is condensed with toluene, a mixture of oligomers A and B is produced.

In stage (c), the desired isomers or isomer mixtures are separated off by distillation and are then conditioned as dielectric fluids. The conditioning of the products for dielectric use is known to the art; it is described at page 4 of EP 8,251. This entails a preliminary purification treatment with alkalis such as NaOH, $Na_2CO_3$ or analogous calcium or potassium compounds at a temperature which can range from 20° to 350° C. A subsequent distillation can sometimes be advantageous. After this preliminary treatment, the following purification stage includes purification with a decolorizing earth or activated alumina, either alone or in combination, depending on the specific techniques employed which are known to the art of dielectric fluids. Similarly, it may be advantageous to add stablizers of the epoxide type or of another type, such as, for example, tetraphenyltin or anthraquinonic compounds.

It is also within the scope of the present invention to condense mixtures of aromatic halides with mixtures of aromatic compounds in the stage (a).

If the aromatic halides are derived from the aromatic compounds under consideration, for example benzyl chloride and toluene or methylbenzyl chloride ($CH_3C_6H_4CH_2Cl$) and xylene, then partial halogenation of the aromatic compound may be carried out upstream of stage (a). A mixture of aromatic halide and aromatic compound is thus obtained, to which it suffices to add ferric chloride to carry out stage (a) of the process of the invention.

In order to further illustrate the present invention and the advantages thereof, the following specific examples are given, it being understood that same are intended only as illustrative and in no case limitative.

EXAMPLE 1

Into a reactor fitted with rotary stirring means and a condenser, 6 moles of benzyl chloride were introduced over 4 hours into 30 moles of toluene containing 35 g of $FeCl_3$ at a temperature of 105° C. When the introduction of the benzyl chloride was complete, the reaction medium was maintained at 105° C. for an additional 1 h, 30 min. The entire reaction mass was then subjected to a single distillation which made it possible to separate off:

(1) unreacted toluene, under a vacuum of 15 mm of mercury with a base temperature of 105° C. The toluene recovered was colorless, having a purity in excess of 99% according to chromatographic analysis, and contained less than 2 ppm of iron;

(2) the oligomer A as described above, which distilled at 105°-263° C. under a vacuum of 15 mm of mercury. The product obtained (900 g), which was slightly yellow, had the following composition:

| | |
|---|---|
| $n_1 + n_2 = 0$ | 75% |
| $n_1 + n_2 = 1$ | 21% |
| $n_1 + n_2 = 2$ | 4% |

The compound $n_1+n_2=0$ was strictly a mixture of benzyltoluene isomers, in the proportion o/m/p=42.7/6.6/50.7.

The dielectric properties were determined and are reported in the Table of Example 7, column 7.1.

A product obtained in the same manner, but with the following washing operations being performed on the organic phase upon completion of the reaction with benzyl chloride:

2×1,000 cc of 3% hydrochloric acid,

3×1,000 cc of water, had those properties reported in the Table of Example 7, column 7.2.

It was determined that there was no difference in the dielectric properties.

EXAMPLE 2

(Not according to the invention)

The same operation of condensing benzyl chloride with toluene as in Example 1 was carried out, but with 35 g of aluminum chloride replacing the ferric chloride. Upon completion of the reaction with benzyl chloride, the reaction mixture was subjected to a single distillation as in Example 1, which yielded the following products:

(1) unreacted toluene, under a vacuum of 15 mm of mercury with a base temperature of 105° C. This toluene was yellow and contained 3.2 ppm of aluminum. Chromatographic analysis demonstrated that this toluene was very impure and, in particular, contained significant amounts of benzene and xylene;

(2) the distillation of the heavier products was continued by gradually increasing the temperature with a higher vacuum. This distillation was very difficult because continuous decomposition occurred, forming benzene, toluene and xylene, with difficulties in producing the vacuum.

Only 300 g of very strongly colored product were obtained, containing 17 ppm of aluminum and having the following composition:

benzene: 1.3%
toluene: 16.0%
xylene: 7.0%
diphenylmethane: 7.5%
benzyltoluene: 34.0%
benzylxylene: 22.0%

This product was obviously useless for dielectric applications. Furthermore, a very large amount of product remained in the distillation flask in the form of an irrecoverable compact block.

It was thus determined that a crude product of toluene benzylation catalyzed using aluminum chloride could not be distilled without a preliminary washing to remove the catalyst.

EXAMPLE 3

The procedure of Example 1 was repeated, except that a crude product of photochlorination of toluene was employed instead of pure benzyl chloride. For this purpose, 6 moles of chlorine were introduced into 24 moles of toluene under photochemical irradiation at a temperature of 90 C. The reaction product was introduced gradually into 12 moles of toluene containing 35 g of $FeCl_3$ at 105° C. When the reaction was complete, the mixture was distilled as in Example 1, which made it possible to separate off:

(1) unreacted toluene having a purity in excess of 99%, which could be used directly in a fresh synthesis operation;

(2) a mixture of oligomer A and of oligomer B as described above, in the proportion of 97.5/2.5 by weight.

The dielectric properties of the mixture were determined and are reported in the Table of Example 7, column 7.3.

A product obtained in the same manner, but by carrying out washing operations using aqueous hydrochloric acid and water on the organic phase upon completion of the Friedel-Crafts reaction, had the dielectric properties reported in the Table of Example 7, column 7.4. It was again determined that there was no difference in the dielectric properties.

EXAMPLE 4

(Not according to the invention)

The procedure of Example 3 was repeated, but with 35 g of aluminum chloride replacing ferric chloride in the Friedel-Crafts reaction. The reaction mixture was then subjected to distillation. The difficulties encountered were the same as those encountered in Example 2, and a product was produced that was unsuited for dielectric applications.

EXAMPLE 5

The operation was carried out as in Example 3, except that a mixture of dichlorotoluene isomers was employed (33% of 2,4-; 26.5% of 2,5-; 18.8% of 2,6-; 11.6% of 2,3-; 8.1% of 3,4-). The photochemical reaction of 6 moles of chlorine with 24 moles of dichlorotoluenes was carried out at 120° C. The Friedel-Crafts reaction was then carried out by reacting the photochlorination reaction mixture with 12 moles of dichlorotoluenes in the presence of 20 g of $FeCl_3$ at a temperature of 140° C. The introduction was carried out over 4 h, 30 min, with regular addition of small amounts of $FeCl_3$. The reaction mass was stirred at 140° C. for an additional 1 h, 30 min, and was then subjected to a single vacuum distillation which made it possible to separate off:

(1) unreacted dichlorotoluenes, under a vacuum of 15 mm of mercury with a base temperature of 150.C. The distillate obtained was colorless and contained less than 1 ppm of iron. Chromatographic analysis indicated that the dichlorotoluene content was higher than 99%;

(2) products of the formula:

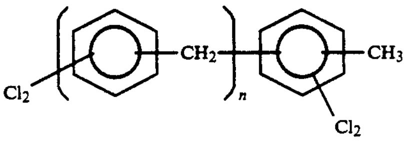

n = 1 97%
n = 2 3%

1,500 g were obtained under a vacuum of 15 mm of mercury with a vapor temperature of 260° to 280° C. It was a slightly yellow liquid containing less than 1 ppm of iron. This product was perfectly suitable for dielectric applications.

A product obtained in the same manner, but with washing of the organic phase resulting from the Friedel-Crafts reaction with aqueous hydrochloric acid and then with water, was identical with that obtained without any washing of the catalyst.

The dielectric properties of these two products (with washing and without washing) were measured as in Example 7; there was no difference whatsoever. Both products were suitable as dielectric materials.

EXAMPLE 6

(Not according to the invention)

The procedure of Example 5 was repeated, but with 35 g of aluminum chloride replacing the ferric chloride. Upon completion of the Friedel-Crafts reaction, the product was subjected to a single distillation to separate off:

(1) unreacted dichlorotoluenes, under a vacuum of 15 mm of mercury with a base temperature of 150° C. The distillation was very difficult to carry out because of the generation of foam due to decomposition reactions. The dichlorotoluenes obtained were highly colored and contained 95 ppm of aluminum. According to GC analysis, the purity was only 85% (contained 10% of light products and 5% of heavy products);

(2) heavier products: as the temperature was gradually increased to 240°-280° C., whitish deposits appeared, and the highly colored distillate thickened and only 1,200 g of product were obtained, containing at least 10% of lighter fraction (dichlorobenzenes and dichlorotoluenes generated by decomposition) and 170 ppm of aluminum.

This product was quite obviously unsuited for dielectric applications.

A large amount of product remained at the bottom of the flask, in the form of an irrecoverable black compact block.

It was thus determined that the desired products could not be obtained without a preliminary washing of the reaction mixture to remove the aluminum chloride.

EXAMPLE 7

Dielectric Properties

These were measured using aging tests in a cell at 100° C.

The samples were treated overnight at room temperature with 3% of activated Tonsil 13, after adding 1% of DGEBA epoxide (bisphenol A diglycidyl ether).

The filtered samples were placed in cells for measuring tan δ (2 cells per sample). These cells were placed in an over at 100° C. and tan δ was monitored for 500 hours.

The results obtained, reported in the Table below, evidenced that the four products had an equivalent stability.

TABLE

| | tan δ × $10^{-4}$ (100° C.) | | | | | | | |
|---|---|---|---|---|---|---|---|---|
| | 7.1 | | 7.2 | | 7.3 | | 7.4 | |
| Time | 1 | 2 | 1 | 2 | 1 | 2 | 1 | 2 |
| 0 | 1.4 | 2.1 | 2.0 | 1.7 | 1.9 | 1.9 | 1.6 | 2.1 |
| 30 min | 1.2 | 1.9 | 1.9 | 1.5 | 1.8 | 1.7 | 1.5 | 1.9 |
| 18 h | 1.5 | 1.8 | 1.9 | 1.7 | 1.7 | 1.7 | 1.6 | 1.8 |
| 41 h | 1.8 | 2.4 | 2.1 | 2.0 | 2.0 | 2.2 | 1.9 | 2.3 |
| 140 h | 2.3 | 2.7 | 2.0 | 2.4 | 3.0 | 1.9 | 2.4 | 2.9 |

TABLE-continued

| | tan δ × $10^{-4}$ (100° C.) | | | | | | | |
|---|---|---|---|---|---|---|---|---|
| | 7.1 | | 7.2 | | 7.3 | | 7.4 | |
| Time | 1 | 2 | 1 | 2 | 1 | 2 | 1 | 2 |
| 210 h | 2.4 | 3.0 | 2.5 | 2.7 | 2.9 | 3.0 | 2.8 | 3.0 |
| 260 h | 2.6 | 3.3 | 3.0 | 3.5 | 3.6 | 5.0 | 3.1 | 4.2 |
| 310 h | 3.4 | 3.9 | 4.1 | 4.0 | 4.9 | 5.5 | 3.9 | 5.0 |
| 370 h | 4.2 | 5.0 | 4.6 | 4.9 | 5.5 | 5.7 | 4.8 | 5.9 |
| 440 h | 5.6 | 6.0 | 6.1 | 5.9 | 6.5 | 6.0 | 5.9 | 6.6 |
| 510 h | 9.3 | 10.6 | 9.0 | 10.9 | 8.5 | 9.6 | 7.7 | 11.0 |
| Stop | | | | | | | | |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a dielectric liquid, comprising (a) Friedel-Crafts condensing at least one aromatic halide with at least one aromatic compound in the presence of a catalytically effective amount of ferric chloride, said aromatic compound being different than said aromatic halide, and thereafter deliberately avoiding any downstream destruction/neutralization and/or washing of said ferric chloride catalyst, and (b) recovering from the medium of reaction a dielectric liquid.

2. The process as defined by claim 1, said at least one aromatic halide comprising benzyl chloride.

3. The process as defined by claim 1, said at least one aromatic compound comprising toluene.

4. The process as defined by claim 1, said at least one aromatic halide comprising an admixture of benzyl chloride and benzylidene chloride.

5. The process as defined by claim 1, said at least one aromatic halide comprising a compound of the formula:

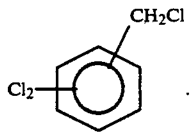

.

6. The process as defined by claim 1, said at least one aromatic compound comprising a compound of the formula:

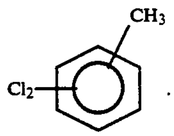

.

7. The process as defined by claim 1, carried out at a temperature ranging from 50° to 150 C.

8. The process of claim 1, wherein after step (a) there is effected an additional step comprising removing unreacted reactants from the medium of reaction.

9. The process of claim 8, wherein said at least one aromatic halide comprises benzyl chloride.

10. The process of claim 8, wherein said at least one aromatic compound comprises toluene.

11. The process of claim 8, wherein said at least one aromatic halide comprises an admixture of benzyl chloride and benzylidene chloride.

12. The process of claim 8, wherein said at least one aromatic halide comprises a compound of the formula:

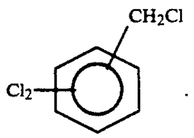

13. The process of claim 8, wherein said at least one aromatic compound comprises a compound of the formula:

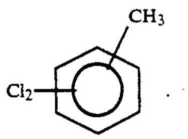

14. The process of claim 8, wherein the process is carried out at a temperature ranging from 50° to 150° C.

15. The process of claim 1, wherein said aromatic halide and said at least one aromatic compound each contain one aromatic ring.

16. The process of claim 8, wherein said aromatic halide and said at least one aromatic compound each contain one aromatic ring.

* * * * *